(12) United States Patent
Cheung et al.

(10) Patent No.: US 7,005,541 B2
(45) Date of Patent: Feb. 28, 2006

(54) LOW WATER METHANOL CARBONYLATION PROCESS FOR HIGH ACETIC ACID PRODUCTION AND FOR WATER BALANCE CONTROL

(75) Inventors: Hosea Cheung, Corpus Christi, TX (US); Michael E. Huckman, Corpus Christi, TX (US); G. Paull Torrence, League City, TX (US)

(73) Assignee: Celanese International Corporation, Dallas, TX (US)

( * ) Notice: Subject to any disclaimer, the term of this patent is extended or adjusted under 35 U.S.C. 154(b) by 486 days.

(21) Appl. No.: 10/328,065

(22) Filed: Dec. 23, 2002

(65) Prior Publication Data

US 2004/0122257 A1   Jun. 24, 2004

(51) Int. Cl.
  *C07C 51/12*  (2006.01)
(52) U.S. Cl. .................................................... 562/519
(58) Field of Classification Search ................ 562/519
  See application file for complete search history.

(56) References Cited

U.S. PATENT DOCUMENTS

| | | | |
|---|---|---|---|
| 3,769,177 A | 10/1973 | Eubanks et al. | |
| 3,769,329 A | 10/1973 | Paulik et al. | |
| 3,791,935 A | 2/1974 | Eubanks et al. | |
| 4,008,131 A | 2/1977 | Price | |
| 5,001,259 A | 3/1991 | Smith | |
| 5,026,908 A | 6/1991 | Smith | |
| 5,144,068 A | 9/1992 | Smith | |
| 5,218,143 A | 6/1993 | Jones | |
| 5,488,153 A | 1/1996 | Baker et al. | |
| 5,760,279 A | 6/1998 | Poole | |
| 5,831,120 A | 11/1998 | Watson | |
| 5,939,585 A | 8/1999 | Ditzel | |
| 6,143,930 A | 11/2000 | Singh et al. | |
| 6,211,405 B1 | 4/2001 | Cheung et al. | |

FOREIGN PATENT DOCUMENTS

| | | |
|---|---|---|
| EP | 0 250 189 B1 | 1/1991 |
| EP | 0 161874 B2 | 7/1992 |
| GB | 2 336 154 A | 10/1999 |

OTHER PUBLICATIONS

Hjortkjaer and Jensen, [Ind. Egn. Chem, Prod. Res. Dev., vol. 16, No. 4, 281-285 (1977)].

*Primary Examiner*—Paul A. Zucker
(74) *Attorney, Agent, or Firm*—M. Susan Spiering

(57) ABSTRACT

The invention relates to a process for the production of acetic acid by carbonylation of methanol, and reactive derivatives thereof, in a reaction mixture using a rhodium-based catalyst in low water conditions. The process is used to achieve reaction rates of at least 15 g mol/l/hr. The high rate reactions proceed at water concentrations of less than 2.0 wt. %. Under certain conditions, the water concentration in the reaction mixture of the process is maintained at a desired concentration by at least one process step including adding a compound such as methyl acetate, dimethyl ether, acetic anhydride, or mixtures of these compounds to the reaction system. The process step of adding the components to the reaction mixture may be combined with other process steps for controlling water concentrations in reaction mixtures for the carbonylation of methanol.

27 Claims, 1 Drawing Sheet

Figure 1:
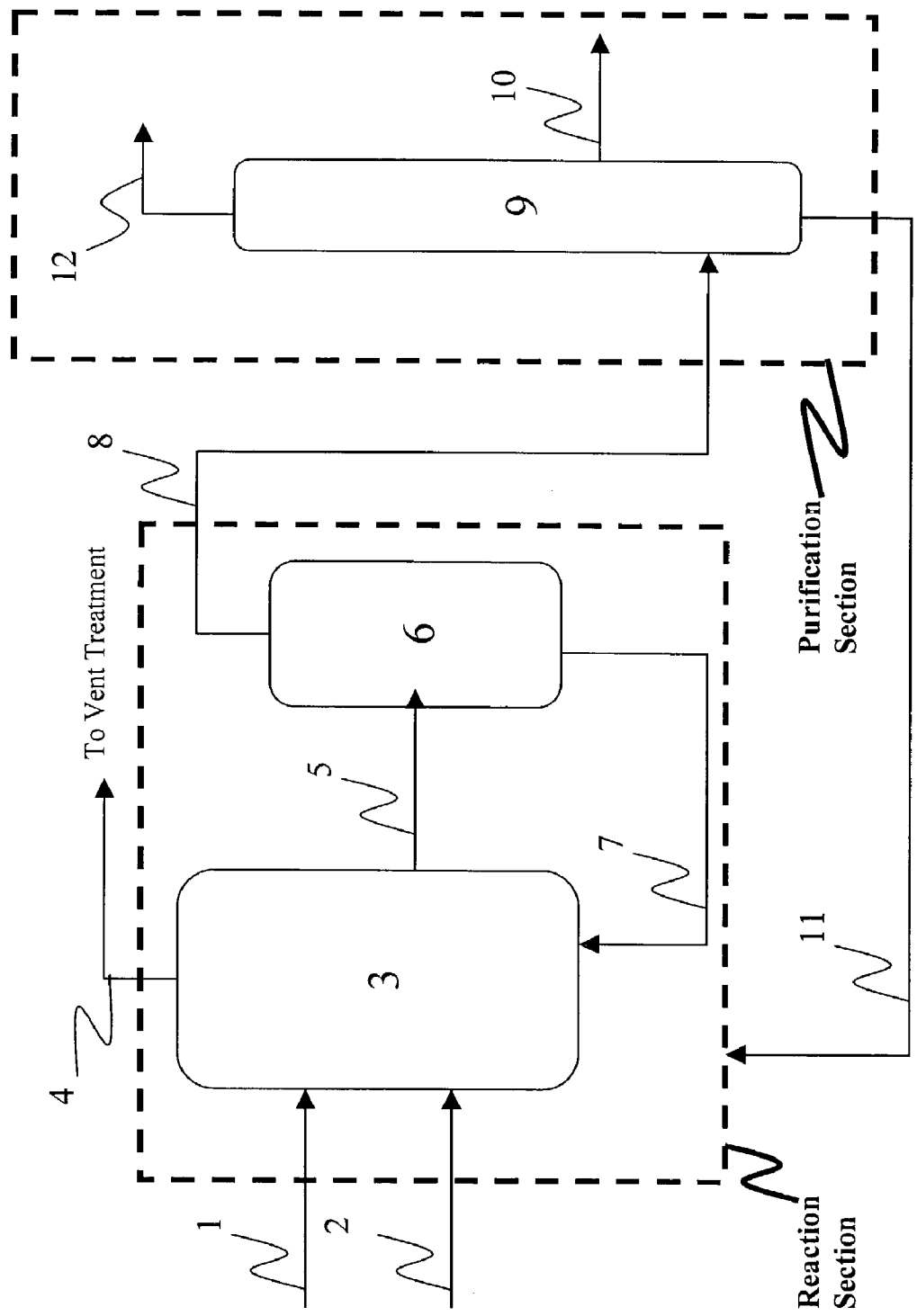

LOW WATER METHANOL CARBONYLATION PROCESS FOR HIGH ACETIC ACID PRODUCTION AND FOR WATER BALANCE CONTROL

BACKGROUND OF THE INVENTION

1. Field of the Invention

This invention relates to an improved method for the manufacture of acetic acid.

2. The Related Art

An important process for the production of acetic acid is the carbonylation of an alkyl alcohol, especially methanol, and reactive derivatives thereof, with carbon monoxide in a liquid reaction medium. Such carbonylation reactions are generally carried out in the presence of a catalyst, e.g., a Group VIII metal catalyst such as rhodium and iridium, a halogen containing catalyst promoter, e.g., methyl iodide, and water. U.S. Pat. No. 3,769,329 discloses the use of a rhodium-based carbonylation catalyst dissolved, or otherwise dispersed, in a liquid reaction medium or supported on an inert solid, along with a halogen-containing catalyst promoter as exemplified by methyl iodide. However, it is understood that various catalyst systems, particularly those incorporating Group VIII metals, may be used for the production of acetic acid through the carbonylation of methanol. Generally, the carbonylation reaction is conducted with the catalyst being dissolved in a liquid reaction medium through which carbon monoxide gas is continuously bubbled. U.S. Pat. No. 3,769,329 discloses that water may be added to the reaction mixture to exert a beneficial effect upon the reaction rate, and water concentrations between about 14 weight percent (wt. %)–15 wt. % are typically used. This is sometimes referred to as the "high water" carbonylation process.

An alternative to the "high water" carbonylation process is the "low water" carbonylation process, as described in U.S. Pat. Nos. 5,001,259, 5,026,908, and 5,144,068. Water concentrations below 14 wt. % can be used in the "low water" carbonylation process. Employing a low water concentration simplifies downstream processing of the desired carboxylic acid to its glacial form. The more water there is in a reaction stream, the greater the operating costs to remove water from the product acetic acid and the greater the capital investment in product recovery and purification equipment. The efficiencies achieved when operating at very low water concentrations makes it attractive to operate at the lowest water concentration possible. However, when reducing the reactor water to minimize operating and fixed costs, it is more difficult to maintain acceptably high rates of acetic acid production with good catalysts stability since the rate of the reaction decreases, as the reactor water is decreased as explained in U.S. Pat. No. 5,026,908.

One of the problems associated with low water production is that catalyst systems, especially rhodium-based catalysts, tend to precipitate out of the reaction mixture when the concentration of water is decreased, especially at concentrations lower than 14 wt. %. Significant catalyst precipitation, of course, can lead to reduced reaction rates, interrupted unit operation, and complete shutdowns. It is known that catalyst stability problems may be minimized by the use of a catalyst stabilizer such as a soluble metal iodide or quaternary iodide salt. As discussed in U.S. Pat. No. 5,218,143, especially suitable salts are the alkali metal iodides such as lithium iodide since these are the most soluble and thermally stable in the reaction medium. EP-A-0161874 describes a reaction system in which an alcohol, as exemplified by methanol, is carbonylated to a carboxylic acid derivative such as acetic acid while using a liquid reaction medium having a low water content. The disclosure describes that this is achieved by the use of defined concentrations of an iodide salt, alkyl iodide and corresponding alkyl ester in the liquid reaction medium to maintain rhodium catalyst stability and system productivity.

An additional problem associated with carbonylation reactions at lower water concentrations is that, even when catalyst systems are stabilized, production rates are adversely reduced. For example U.S. Pat. No. 5,760,279 discloses than when operating under low water conditions, the realized reaction rate may be less than half of what would normally be expected under a given set of conditions.

Various techniques for increasing the production rate under low water carbonylation reaction conditions have been proposed. Production rates are typically defined in terms of space-time yield (STY) which is expressed in gram-moles of acetic acid produced per hour per liter of reaction medium (g-moles/l/hr) contained in the carbonylation reactor. The volume of the reaction medium is being determined at ambient temperature in the unaerated state. U.S. Pat. No. 5,218,143 discloses that production levels may be enhanced at low water levels if the reactor is operated with optimized concentrations of methyl acetate in the reaction mixture. EP-0-250189 proposes to add hydrogen gas in the carbon monoxide feed to the reaction mixture to enhance the production rate. U.S. Pat. No. 5,939,585 discloses the use of ruthenium or osmium as catalyst promoters to enhance production rates. The disclosure of this patent indicates the use of such promoters may result in STY's of up to approximately 11 g-mol/l/hr under low water conditions at concentrations of less than 1.0 wt. % water. U.S. Pat. No. 5,218,143 discloses the use of Group VIB metal catalyst co-stabilizers for increasing STY's under low water conditions to as high as 9.2 g-mol/l/hr at a water concentration of 2.0 wt. %. U.S. Pat. No. 5,760,279 indicates that the incorporation of a manganese stabilizer in conjunction with a rhodium catalyst may increase STY's up to approximately 8 g-mol/l/hr at a water concentration of 4.5 wt. %. U.S. Pat. No. 5,488,153 and GB 2,336,154 A propose the use of bidentate phosphorus-sulfur ligands coordinated to rhodium catalysts for increasing reaction rates under low water conditions. The examples of U.S. Pat. No. 5,488,153 disclose the achievement of production rates up to an STY of 19.6 g-mol/l/hr. GB 2,336,154 A discloses reaction rates as high as 21.9 g-mol/l/hr. These reactions disclosed in these references take place under high water conditions.

While some of the above references refer to rhodium catalyst concentrations as high as 5000 ppm, the examples in these references generally disclose rhodium catalyst concentrations of about 1000 ppm or less.

U.S. Pat. No. 5,144,068 discloses that, at low water concentrations, there is a synergy between the methyl acetate and iodide salt stabilizer in the carbonylation reactor to enhance methanol carbonylation. It also discloses that an advantage of operating the reactor at high methyl acetate concentrations is a reduction in the formation of undesirable reaction products. In particular, propionic acid is reduced by an order of magnitude. Carbon dioxide and hydrogen, which are formed by the water gas shift reaction, are also reduced.

Because the carbonylation rate of reaction is strongly dependent on water concentrations, it is important to maintain water levels in the reaction mixture during the production of acetic acid within controlled ranges to maintain high reaction rates. Hjortkjaer and Jensen [Ind. Eng. Chem., Prod. Res. Dev. 16, 281–285 (1977)] discloses the strong dependence of the rate of reaction on water levels by demonstrating that the reaction rate increases as water concentration is increased up to 14 wt. %. The control of water in the reaction mixture can be affected, at least in part, by two key reactions in the reaction mixture. The first reaction produces water through methanation in accordance with the following formula:

$$CH_3OH + H_2 \rightarrow CH_4 + H_2O$$

The second reaction which consumes water is known as the aforementioned water gas shift reaction shown by the following formula:

$$CO + H_2O \rightarrow CO_2 + H_2$$

To effectively control water in the reaction medium, it is important to know which reaction predominates in order to define a water supply or water removal operation from the reaction section to maintain an accurate water balance within the reaction section to minimize changes in reaction carbonylation rates as a result of changes in the reactor water concentration.

U.S. Pat. No. 5,831,120 discloses that in iridium-catalysed carbonylation reactions, the generation rate of water by the methanation reaction is relatively high and can be greater than the rate of consumption of water by the water gas shift reaction. In this situation there is a need to remove excess water generated by the imbalance. In contrast, U.S. Pat. No. 5,831,120 also discloses that in rhodium-catalysed carbonylation reactions, the methanation reaction is relatively slow compared to the rate of the water gas shift reaction so water is consumed in the reaction system. It is typically necessary to provide water to the rhodium-catalysed system to maintain a steady-state concentration of water in the reaction mixture.

Various means have been proposed for removing excess water from crude product streams produced in carbonylation reaction systems. U.S. Pat. Nos. 3,769,177 and 3,791,935 disclose the removal of water from reaction systems through a series of distillations. U.S. Pat. No. 4,008,131 discloses a modification of such systems by using a sidestream for removal of water from a distillation column. The purported advantage of such a system is to minimize the removal of valuable methyl iodide with the water when it is removed from the overhead from a distillation column. The process systems disclosed in these patents are directed to means for removing water from crude product streams in the post reaction section portions of the process systems. Therefore, the disclosed systems do not address controlling water in the reaction section of carbonylation process systems.

U.S. Pat. No. 5,831,120 discloses the removal of excess water in an iridium-catalysed system by a combination of removing and disposing of water from the overhead of a light ends distillation column and replacing a portion of the methanol feed into the reaction mixture with a component selected from the group of methyl acetate, dimethyl ether, acetic anhydride and mixtures thereof. The patent discloses that dimethyl ether and methyl acetate are carbonylated to produce acetic acid with a net consumption of water and acetic anhydride removes water from the reaction mixture by reaction to produce acetic acid. In this process, water is thought to be consumed in accordance with the following formulas:

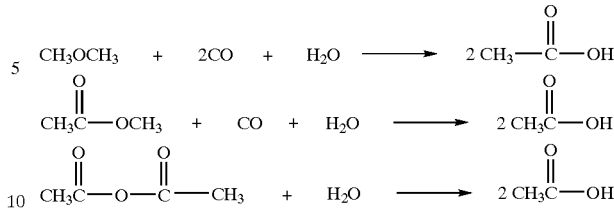

U.S. Pat. No. 5,001,259, and related U.S. Pat. Nos. 5,026,908, and 5,144,068 disclose rhodium catalysed low water carbonylation processes in which high methanol carbonylation rates are achieved while the reaction section water concentrations are maintained at very low levels from a finite ($\leq 0.1$ wt. %) water concentration to high water concentrations. These patents disclose that the reaction medium concentration is maintained by controlling the flow of carbon monoxide, water, methanol, and methyl iodide. The highest acetic acid production reaction rate disclosed in these patents is an STY of approximately 32 at a water concentration of 2 wt. %. However, at water concentrations of less than 2 wt. %, the highest acetic acid STY disclosed is approximately 12. FIG. 10 of these patents demonstrates the difficulty of maintaining favorable reaction rates at water concentrations below 2.0 wt. %. As seen in FIG. 10, the reaction rate drops precipitously as the water concentration goes below 2.0 wt. %.

In summary, the state of the art in carbonylation technology still lacks a method for maintaining a highly stable catalyst system, in controllable low water conditions, useful for achieving reaction rate STY's of 15 g-mol/l/hr and higher at water concentrations of less than 2 wt. %.

SUMMARY OF THE INVENTION

The present invention relates to processes for the production of acetic acid by carbonylation of alkyl alcohols, reactive derivatives of alkyl alcohols, and mixtures of alkyl alcohols and reactive derivatives thereof in a reaction mixture with low water content. In addition to producing acetic acid under low water conditions, the present invention provides high acetic acid production rates. An additional feature of the present invention is the maintenance of the low water concentration in controlled ranges while operating at high production rates. The present invention achieves acetic acid production rates of 15 g-mol/l/hr and higher under water concentrations in the reaction mixture of less than 2.0 wt. %. The process of the present invention uses high levels of rhodium or rhodium/iridium catalyst systems with high levels of methyl acetate. Under certain conditions, the water concentration in the reaction mixture of the process is maintained at the desired concentration by at least one process step comprising adding to the process a water consuming component such as dimethyl ether, methyl acetate, acetic anhydride, or mixtures of these compounds. The step of adding the water-consuming component to the reaction mixture may be combined with other process steps for controlling water concentrations in carbonylation reaction mixtures.

DRAWING

FIG. 1 is a schematic diagram of an embodiment of the process of the present invention.

DETAILED DESCRIPTION OF THE INVENTION

While from a cost standpoint, it is desirable to operate carbonylation processes at low water conditions in the reactor, it is well known, as discussed in U.S. Pat. No. 5,144,068, that under low water conditions, the production yields of such processes can be considerably lower than would be expected while operating at higher water concentrations, with other conditions being similar. However, the present invention is able to achieve unexpectedly high reaction rates while at the same time operating under and capturing the cost advantages of water concentrations of less than 2 wt. % in the reaction mixture. The present invention is able to attain these high production rates by optimizing key reaction components of rhodium or rhodium/iridium based catalyst systems while at the same time maintaining very low water concentrations within efficient ranges.

The present invention relates to low water carbonylation processes with high production rates. Contrary to previous understandings, it has been discovered that reaction rates may be brought to and maintained at very high levels through the use of high catalyst concentrations by using the synergism of the iodide salt co-promoter with the methyl acetate in particular at high methyl acetate concentrations with high catalyst concentrations. Under certain conditions, these processes may produce water during the carbonylation reaction. That is to say, the production of water through the above-identified methanation reaction exceeds the consumption of water through the discussed water gas shift reaction. The present invention recognizes these conditions and provides a method for maintaining water balance in the reaction mixtures during such conditions while maintaining high reaction rates.

Processes for the synthesis of acetic acid by the catalytic carbonylation of methanol with carbon monoxide are well known in the art as exemplified by the disclosures of the previously cited references. Carbon monoxide is reacted with methanol and/or reactive derivatives thereof in the presence of a catalyst system which may comprise, for example, a Group VIII metallic element, particularly Rh, Ir, Co, Ni, Ru, Pd or Pt, and most often Rh or Ir, a halogen promoter, most often a hydrogen halide or organic halide, particularly an alkyl iodide such as methyl iodide, a stabilizer/copromoter, which is a salt of a metal of Group IA or IIA of the Periodic Table, or a quatenary ammonium or phosphosium salt, particularly an iodide or acetate salt and most often lithium iodide, or lithium acetate. The active catalyst may be a complex of the Group VIII metal, and in some cases may be added to the reaction section as a pre-formed complex rather than the described individual catalyst components. The catalyst system is dissolved or dispersed in a liquid medium comprising methyl acetate, acetic acid, a finite amount of water, e.g., at least about 0.1 wt. % and any other solvent component compatible with the other compounds present. Suitable derivatives of methanol for use in the carbonylation reaction include methyl acetate, dimethyl ether and methyl iodide.

Suitable catalyst systems for the processes of the present invention comprise rhodium and rhodium/iridium metals and compounds as the Group VIII metal and an alkyl iodide as a halogen promoter. The concentration of the alkyl iodide, usually methyl iodide, in the reaction medium is typically between about 2.0 and about 30 wt %, with one embodiment between about 5.0 and about 15 wt. %, and still another embodiment between about 5 and about 10 wt. %. A catalyst stabilizer/co-promoter may be used as well. The stabilizer/co-promoter may be in the form of a soluble salt from an alkali metal or alkaline earth metal or a quaternary ammonium or phosphonium salt which generates an effective amount as defined above of iodide ion in the reaction solution. The catalyst stabilizer/co-promoter is preferably lithium iodide, lithium acetate or mixtures thereof. The catalyst system can further comprise a transition metal salt as a co-promoter selected from the group consisting of salts of ruthenium, tungsten, osmium, nickel, cobalt, platinum, palladium, manganese, titanium, vanadium, copper, aluminum, tin, and antimony. The concentration of the iodide ion in the reaction medium is generally between about 2.0 and about 20 wt. %. In one embodiment, it is present between about 5.0 and about 20 wt. % and in another embodiment the iodide ion is present from about 10 to about 20 wt. %. All of these reaction components are dissolved or dispersed in a medium comprising methyl acetate, acetic acid, and a low concentration of water. The concentration of methyl acetate in the reaction medium is generally between about 1.0 and about 30 wt. %, with one embodiment between about 2.0 and about 15 wt. % with still another embodiment wherein methyl acetate is present from about 3.0 to about 10 wt. %. Rhodium catalyst systems are well known. Suitable catalyst systems comprising rhodium as the Group VIII metal are exemplified in U.S. Pat. No. 3,769,329. Catalyst systems employing a rhodium salt combined with an iridium salt are also known. Suitable rhodium/iridium catalyst systems are exemplified in U.S. Pat. No. 6,211,405. Rhodium-based catalyst systems and rhodium/iridium based catalyst systems are referred to hereinafter as rhodium-based catalyst systems. For purposes of this application Group VIII metals shall refer to the identified Group VIII metals and chemical compounds incorporating the identified Group VIII metals.

During a period of active reaction, methanol and carbon monoxide are continuously fed to a reactor containing reaction liquid in which a desired partial pressure of carbon monoxide is maintained. As mentioned previously and discussed hereinafter, the reaction liquid may contain small amounts of undesirable impurities in addition to the desired components identified previously, e.g., acetaldehyde and other carbonyl containing permanganate reducing compounds ("PRC's"), and propionic acid. PRC's are defined herein as carbonyl compounds, such as acetaldehyde, which leads to formation of unsaturated aldehydes and other carbonyl impurities such as acetone, methyl ethyl ketone, butyraldehyde, crotonaldehyde, 2-ethyl crotonaldehyde, 2-ethyl butyraldehyde and the like, and the aldol condensation products thereof. Other PRC's include alkyl iodides, such as ethyl iodide, propyl iodide, butyl iodide, pentyl iodide, hexyl iodide and the like.

To prevent the accumulation of inert compounds or agents, a gaseous purge is withdrawn from the top of the reactor and treated to recover valuable condensables such as methyl iodide and methyl acetate before flaring. Reaction liquid is withdrawn from the reactor and fed to a flasher where a reduction in pressure results in the vaporization of the lighter components from the reaction mixture and product acetic acid, the remainder of the reaction mixture comprising mostly acetic acid and the catalyst may be recycled to the reactor. The vapors from the flasher are fed to a light ends or splitter column from which a crude acetic acid product is withdrawn as a liquid side draw or base product, as described in U.S. Pat. No. 5,144,068, and sent to further purification and the overhead vapors are condensed and separated into a light aqueous phase and a heavy organic phase. The light aqueous phase contains a preponderance of water, a lower but significant amount of acetic acid, and much smaller amounts of methanol, methyl iodide, and methyl acetate. Acetaldehyde and other PCR's, which are by-products of the initial reaction, or are formed subsequently from further reaction of acetaldehyde, are also present. The heavy organic phase contains predominately methyl iodide with some methyl acetate, a minor amount of water, and a typically smaller percentage of acetaldehyde, than the light aqueous phase. The heavy organic phase is either recycled directly to the reaction section or recycled after further processing.

The light aqueous phase of the overhead condensate of the light ends column is typically used as reflux and a portion is recycled directly to the reaction section. As used herein, the phrase "reaction section" refers to the reactor and flasher components of the system collectively. In some processes, the light aqueous phase is first fed to an acetaldehyde removal system as disclosed, for example, in U.S. Pat. Nos. 6,143,930 and 3,769,329. In one variation of an acetaldehyde removal system the light aqueous phase of the light ends column overhead condensate is fed to a first distillation column, termed an "acetaldehyde concentrator", which serves to separate most of the acetaldehyde, methyl iodide, and methyl acetate as overhead from a heavier fraction comprising acetic acid and water, which is recycled to the purification section. The latter overhead is then fed to a second distillation column, termed an "acetaldehyde stripper", which serves to separate most of the acetaldehyde in this stream, from a heavier fraction comprising methyl iodide and methyl acetate, which is recycled to the purification section. The latter overhead comprising an increased concentration of acetaldehyde and some heavier components such as methyl iodide is then subjected to an extraction with water to obtain an aqueous extract comprising most of the acetaldehyde and an organic raffinate comprising the less water-soluble components of the stream such as methyl iodide, which is recycled to the purification section. The aqueous acetaldehyde stream is disposed of as waste. As used herein, the phrase "purification section" refers to the distillation and separator/decanter components of the system collectively.

The continuous carbonylation process may be thought of as comprising three basic sections: the reaction, purification, and off-gas treatment sections. Referring to FIG. 1, continuous streams of an alkyl alcohol and/or reactive derivatives thereof and carbon monoxide are fed through lines 1 and 2 respectively into stirred reactor 3, or other suitable reactor, containing a reaction liquid comprising an acetic acid solution of a rhodium-based catalyst system, a halogen promoter, a copromoter/stabilizer, water, unreacted alkyl alcohol and/or reactive derivatives thereof and carbon monoxide, and impurities such as acetaldehyde and other PRC's, and higher alkyl iodides. Gases formed in the reaction section are withdrawn through line 4 and are sent to vent recovery for the separation of components suitable for recycle to the reaction. Reaction liquid is continuously withdrawn from reactor 3 through line 5 and is fed to flasher 6 where a reduction of pressure causes a portion of the acetic acid and most of the lower boiling compounds to be flashed off as vapor leaving a solution of the heavier components of the catalyst system. The liquid remaining in flasher 6 is recycled through line 7 to reactor 3 while the vapors from flasher 6 are fed through line 8 to light ends or "splitter" column 9 where most of the lower boiling components including methyl iodide, methyl acetate, and acetaldehyde, and a portion of the water are removed overhead. A crude aqueous acetic acid liquid is withdrawn from light ends column 9 through line 10 and sent to the acetic acid recovery system (not shown). A bottoms fraction comprising some acetic acid and higher boiling components is withdrawn from light ends column 9 through line 11 and recycled to the reaction section. The overhead vapor stream from the light ends column is condensed and fed through line 12 for further processing in accordance with a variety of known additional processing steps. A portion of this further processed stream (not shown) containing methyl iodide, methyl acetate, and some acetic acid is recycled to the reactor or purification section.

In some chemical processes, it is necessary to monitor the progress of the chemical reaction and to adjust the supply of the reactants to ensure that the reaction proceeds as desired. The production of acetic acid is one such chemical process. One method of manufacturing acetic acid, by carbonylation of methanol or its derivatives, such as methyl acetate or methyl iodide, involves a chemical reaction initiated by a catalyst system as described previously. Carbonylation has become a preferred route to make acetic acid. Nevertheless, there are countervailing considerations which affect implementation of this process. First, the underlying reaction chemistry is intricate, involving a number of interrelated reactions, by-products and equilibriums, all of which must be properly balanced, one against the other, to make the process practicable and maximize efficiency of raw material utilization. Also, the catalyst systems required for carbonylation are generally expensive. Moreover, carbonylation catalyst systems are extraordinarily sensitive to changes in any number of reaction parameters, which, in turn, adversely affect catalyst stability and activity.

It is desirable to produce acetic acid at low water concentrations in reaction mixtures to provide for greater system efficiency and productivity. Employing a low water concentration simplifies downstream processing of the desired carboxylic acid to its glacial (i.e., highly pure) form. It is recognized that water is an undesirable component of crude acetic acid and the more water there is in the crude product stream, the greater the operating costs and required capital investments in the reaction and product recovery purification systems. To accommodate for the system volume occupied by water and to remove the water in a high water process can be a major capital and energy expenditure as well as system capacity limiting. However, it is generally found that the lower the water concentration, the carbonylation rate decreases. For example, at water concentrations approaching 5.0 wt. %, the carbonylation reaction rate decreases significantly because the reaction rate is highly dependent on reactor water, especially at very low water concentrations. It becomes critical to maintain a tight water balance around the reaction system and for that matter within the reaction section, to maintain high reactor activity and therefore high production rates.

The present invention provides a process by which reaction rates may be maintained at high levels even as the water content in the reaction mixture is maintained at less than 2.0 wt. %. The present invention provides stable reaction rates with STY's of at least 15 g-mol/l/hr with water concentrations less than 2.0 wt. % and rhodium concentrations attributable to rhodium-based catalyst systems of at least 1000 ppm in the reaction mixture. In one embodiment of the present invention, the reaction rate is an STY of about 20 to about 40 g-mol/l/hr with a reaction mixture water content of less than 2.0 wt. %. In another embodiment, the STY's range from 25 to 40 g mol/l/hr at a reaction mixture water content of less than 2.0 wt. %. In still another embodiment, the STY's, with reaction mixture water content of less than 2.0 wt. %, in accordance with the present invention, range from about 35 to about 40 g-mol/l/hr.

The present invention achieves these previously unobtainable reaction rates at such low water concentrations by a combination of optimizing reaction parameters such as catalyst concentration, methyl acetate concentration, and reaction temperature, etc., while maintaining a narrow water balance in the reaction mixture. It has been discovered that very high catalyst concentrations of rhodium-based catalyst concentrations in combination with high methyl acetate concentrations may be used to achieve such high reaction rates.

Generally, the higher the rhodium-based catalyst concentration in the reaction mixture, the higher the reaction rate that may be achieved, especially at low water concentrations. In one embodiment of the present invention the water concentrations less than 2.0 wt. % with a rhodium or rhodium/iridium concentration of at least 1000 ppm and an STY of 15 to about 20 g-mol/l/hr. In another embodiment of the present invention the water concentrations is less than 0.7 wt. % with a rhodium/iridium concentration of at least 1500 ppm and an STY of about 20 to 30 g-mol/l/hr. In still another embodiment of the present invention, the water concentration is less than 0.5 wt. % with a rhodium/iridium concentration of at least 1800 ppm and an STY of about 30 to about 40 g mol/l/hr.

The rhodium-based catalyst systems useful in the present invention are used in combination with a catalyst stabilizer such as soluble metal iodide or quaternary iodide salt. A suitable catalyst promoter is methyl iodide present in concentrations ranging from about 2 wt. % to about 30 wt. %. In one embodiment the methyl iodide concentration ranges from about 5 wt. % to about 15 wt. %. In another embodiment, the methyl iodide concentration range is from about 5 wt. % to about 10 wt. %.

The methyl acetate concentration in the reaction mixture ranges from about 1 wt. % to about 20 wt. % in one embodiment. In another embodiment, the methyl acetate concentration ranges from about 2 wt. % to about 15 wt. %. In still another embodiment of the present invention, the range of the methyl acetate concentration is from about 3 wt. % to about 10 wt. %.

An important factor in operating at the high reaction rates in accordance with the present invention is the ability to maintain a stable reaction mixture composition by maintaining water concentration within a tight or narrow range at the very low water concentrations in accordance with the present invention. It has been unexpectedly discovered that under certain circumstances while the carbonylation proceeds at reaction rates in accordance with the present invention, the water balance of the reaction system may deviate from expected water balance mechanisms. To maintain high carbonylation reaction rates in accordance with the present invention, it is important to recognize when a particular reaction is water producing or water consuming. As disclosed in the previously discussed U.S. Pat. No. 5,831,120, among those skilled in the art, it was thought that rhodium catalyst systems, when used in carbonylation reactions, result in a net consumption of water in the catalyst reaction mixture. In order to maintain a stable water concentration in the rhodium-based reaction mixture, it was previously thought necessary to add water to the reaction mixture since the water gas shift reaction is greater than the methanation reaction. However, it has been discovered that under certain circumstances, rhodium-based catalyst systems produce carbonylation reactions which are net producers of water since the methanation reaction is greater than the water gas shift reaction. Under these circumstances, to maintain a steady water concentration in the reaction mixture to achieve a stable and productive reaction, it is necessary to eliminate the excess water. This may be accomplished by either mechanically or physically or by chemically removing the water from the reaction mixture or to consume the water through chemical pathways.

To detect when the net production of water occurs, it is necessary to monitor the STY's of both carbon dioxide and methane in the reactor. Monitoring these production rates provides an assessment of the net water production mechanism ongoing in the reaction mixture. In rhodium-based catalyst carbonylation reactions with high concentrations of catalyst and high methyl acetate concentrations at low reactor water conditions, the production of methane in the reaction may exceed the production of carbon dioxide and the reaction system becomes water producing rather than water consuming. This change to an overall water producing reaction system was unexpected and surprising. This occurs because, at certain conditions, the methanation reaction represented by the equation: $CH_3OH + H_2 \rightarrow CH_4 + H_2O$ dominates (reaction is greater than) over the water gas shift reaction represented by the equation: $CO + H_2O \rightarrow CO_2 + H_2$.

As mentioned above, these findings are unexpected and contrary to results reported in U.S. Pat. No. 5,831,120 in which it is stated that in rhodium only catalysed reaction systems, there is typically the need to add water to the system. It is found that varying the water, methyl acetate, and rhodium concentrations, that carbonylation reactions which are water producing may occur over a water concentration range of about 0.1 wt. % to 4.0 wt. %.

EXAMPLES

The Examples set forth in the following Table and related discussion provide exemplary demonstrations of carbonylation reactions in accordance with the present invention in which reaction rates exceed 15 g-mol/l/hr under water concentrations of less than 2.0 wt. %. An experimental unit was employed and brought to a steady state. Conditions are as noted in Table I.

TABLE I

| | Reaction Conditions | | | | | Process Rates | | |
| --- | --- | --- | --- | --- | --- | --- | --- | --- |
| Example | $H_2O$ Wt. % | MeOAc wt. % | MeI wt. % | Rh ppm | $H_2$ psi | Acid STY | $CO_2$ STY | $CH_4$ STY |
| 1 | 0.4 | 3.7 | 6.4 | 1613 | 11 | 28 | 0.01 | 0.03 |
| 2 | 0.5 | 5.6 | 6.7 | 1897 | 12 | 40 | 0.01 | 0.01 |
| 3 | 0.7 | 5.8 | 6.1 | 1793 | 12 | 36 | 0.01 | 0.03 |
| 4 | 0.7 | 6.0 | 6.7 | 1387 | 14 | 24 | 0.01 | 0.02 |

1. Reactor conditions for Examples 1–4 are 195° C., 400 psig.
2. All STY values provided in g-mol/l/hr.
3. All reactions in Examples were at 10 wt. % lithium iodide.

These Examples demonstrate conditions under which the rate of the methanation reaction exceeds the rate of the water gas shift reaction or the rates are the same. By reviewing the $CH_4$ and $CO_2$ STY's of the Examples, one sees in Example 2, there is neither a net production nor a net consumption of water in this reaction since the $CO_2$ STY equals the $CH_4$ STY. Conversely, in Examples 1, 3, and 4, the rate of the methanation reaction as indicated by the $CH_4$ STY exceeds the rate of the water gas shift reaction as indicated by the $CO_2$ STY. It is important to remember that depending on the reaction concentrations at water concentrations below 2 wt. %, either reaction can predominate to affect the reaction water concentration which in turn will affect the acetic acid production rates of the process. In Examples 1, 3, and 4, there is a net production of water in the reaction mixture and this water must be removed to maintain the low water concentration at the high reaction rates in accordance with the present invention.

Suppression of the water gas shift reaction in favor of the methanation reaction resulting in a net balance of water production may be experienced over a range of water concentrations, rhodium-based catalyst concentrations, and concentrations of other components such as methyl acetate, and methyl iodide. For example, a net production of water may develop at low water conditions of less than 2.0 wt. % while operating at reaction rates of at least 15 g mol/l/hr and with rhodium-based catalyst concentrations of at least 1000 ppm. The net production of water is more likely to occur at water concentrations of less than 1.0 wt. %, rhodium-based catalyst concentrations of at least about 1200, with reaction rates of at least about 25 g mol/l/hr. The net production of water is still more likely to occur at water concentrations of less than about 0.5 wt. %, rhodium-based catalyst concentrations of at least about 1500 ppm, with reaction rates of at least about 30 g mol/l/hr.

While producing acetic acid under conditions in which there is a net water production, there is a need to eliminate the excess water produced in order to maintain the desired low reaction water concentrations. The water may be removed mechanically or by chemical pathways in accordance with the present invention. If mechanical removal of the water is chosen, the water may be removed by a variety of techniques known in the art for removal of water from reaction systems operating at conditions different from the present invention. Some of the various techniques for removal of the excess water are disclosed in U.S. Pat. Nos. 4,008,131, 3,791,935, 3,769,117, and the other methods disclosed or referred to in 5,831,120.

However, methods of mechanically removing water have many shortcomings, including the requirement of additional capital expenditure. Although the use of such mechanical water removal systems are within the contemplation of the present invention, it has been discovered that in high reaction rates under low water conditions in accordance with the present invention, the excess water may be removed entirely by chemical pathways. A combination of the mechanical water removal process and the removal of water by chemical pathways is also within the contemplation of the present invention.

In the processes of water removal by chemical pathways, the excess water may be removed by adding methyl acetate, dimethyl ether, acetic anhydride, or mixtures of these compounds to the reaction section. The addition of one of these compounds to the reaction section reduces the water concentration in the reaction section. Dimethyl ether and methyl acetate are carbonylated to produce acetic acid with a net consumption of water in the process. The addition of acetic anhydride reduces the concentration of water in the reaction section through a reaction of acetic anhydride and water to produce two moles of acetic acid, as set forth in the earlier equation. The temperature and the nature of the catalyst solution in the reaction zone and the flasher zone are sufficient to rapidly hydrolyze the acetic anhydride.

The amount of the water-consuming agent added to the reaction section is dependent on the rate of the net water production determined by the relative rates of the methanation and water gas shift reactions in the reactor zone. However, generally, the amount of water consuming agent added should be at least stoichiometric with the water produced in the carbonylation reaction in accordance with the equations shown above. The water-consuming agent may be introduced at various locations in the process. For example, the water-consuming agent may be introduced into the reactor zone, flasher zone, or in the purification zone as long as it is eventually recycled to the reactor. However, introduction of the water-consuming agent may be conveniently accomplished also by introducing it into the methanol feed. It is understood that reference to adding the water consuming agent to the reaction section includes additions to streams of the process that are ultimately recycled to the reaction section as well as additions directly to the reaction zone or flasher zone.

It has been discovered that the addition of water consuming agents to the reaction section in accordance with the present invention is useful in rhodium-based catalyst reactions at water concentrations above 2.0 wt. %. This method of water balance control is satisfactory in reaction systems using rhodium-based catalyst systems at water concentrations up to 5.0 wt. % in the reaction mixture.

All patents and publications referred to herein are hereby incorporated by reference in their entireties.

Although the present invention and its advantages have been described in detail, it should be understood that various changes, substitutions, and alterations could be made herein without departing from the spirit and scope of the invention as defined by the following claims.

We claim:

1. A process far the production of acetic acid at a space-time yield of at least 15 g-mol/l/hr, by a catalytic carbonylation reaction, comprising reacting a compound selected from the group consisting of an alkyl alcohol and reactive derivatives thereof, in the presence of carbon monoxide and a rhodium-based catalyst system in a reaction mixture wherein the reaction mixture comprises less than 2.0 wt. % water, at least 1000 ppm of a metal selected from the group consisting of rhodium, and combination of rhodium and iridium, an iodide ion at a concentration in the range of about 2 to 20 wt. %, and a halogen promoter at a concentration of about 2.0 wt. % to about 30.0 wt. %.

2. The process in accordance with claim 1 wherein the halogen promoter is present at a concentration of about 5.0 wt. % to about 15.0 wt. % of the reaction mixture.

3. The process in accordance with claim 1 wherein the reaction mixture comprises form about 1.0 wt. % to about 30.0 wt. % methyl acetate.

4. The process of claim 3 wherein the halogen promoter is methyl iodide.

5. The process of claim 4 wherein the alkyl alcohol is methanol.

6. The process of claim 5 wherein the reaction mixture comprises less than 0.7 wt. % water and at least 1500 ppm of the rhodium-based catalyst system.

7. The process of claim 5 wherein the reaction mixture comprises less than 0.5 wt. % water and at least 1800 ppm of the a Group VIII metal.

8. The process of claim 5 wherein the space-time yield for the production of acetic acid ranges from about 15 g-mol/l/hr to about 20 g-mol/l/hr.

9. The process of claim 6 wherein the space-time yield for the production of acetic acid ranges form about 30 g-mol/l/hr to about 40 g mol/l/hr.

10. The process of claim 7 wherein the space-time yield for acetic acid production ranges from about 30 g mol/l/hr to about 40 g-mol/l/hr.

11. The process of claim 6 wherein the methyl iodide is present from about 5 wt. % to about 10 wt. % of the reaction mixture.

12. The process of claim 5 wherein carbon dioxide and methane are produced in the reaction mixture and wherein the space-time yield for the production of methane exceeds the space-time yield for the production of carbon dioxide.

13. A process for the production of acetic acid by a carbonylation reaction in a system comprising a reaction section and a purification section, comprising the steps of: (a) reacting a compound selected from the group consisting of an alkyl alcohol and reactive derivatives thereof, with carbon monoxide in the presence of a rhodium-based catalyst system in a reaction mixture having a water content ranging from about 0.1 wt. % to about 5.0 wt. %, an iodide ion at a concentration in the range of about 2 to 20 wt. %, and a halogen promoter at a concentration of about 2.0 wt. % to about 30.0 wt. %, and (b) introducing a compound selected from the group consisting of methyl acetate, dimethyl ether, acetic anhydride, and mixtures thereof into the reaction section.

14. The process of claim 13 wherein the halogen promoter present at a concentration ranging from about 5.0 wt. % to about 15.0 wt. % of the reaction mixture.

15. The process in accordance with claim 14 wherein the reaction mixture comprises form about 1.0 wt. % to about 30.0 wt. % methyl acetate.

16. The process of claim 15 wherein the halogen promoter is methyl iodide.

17. The process of claim 16 wherein the alkyl alcohol is methanol.

18. The process of claim 17 wherein the rhodium-based catalyst system is present in the reaction mixture at a concentration sufficient to yield at least 1000 ppm of a Group VIII metal selected from the group consisting of rhodium, iridium, and blends thereof.

19. The process of claim 17 wherein the rhodium-based catalyst system is present in the reaction mixture at a concentration sufficient to yield at least 1500 ppm of a Group VIII metal selected from the group consisting of rhodium, iridium, and blends thereof.

20. The process of claim 17 wherein the rhodium-based catalyst system is present in the reaction mixture at a concentration sufficient to yield at least 1800 ppm of a Group VIII metal selected from the group consisting of rhodium, iridium, and blends thereof.

21. The process of claim 18 wherein the space-time yield for the production of acetic acid is at least 15 g mol/l/hr.

22. The process of claim 19 wherein the space-time yield for the production of acetic acid is least 20 g-mol/l/hr.

23. The process of claim 20 wherein the space-time yield for the production of acetic acid is at least 30 g mol/l/hr.

24. The process of claim 23 wherein the methyl iodide is present from about 5.0 wt. % to about 10.0 wt. % of the reaction mixture.

25. The process of claim 21 wherein the water concentration in the reaction mixture ranges form about 0.1 wt. % to about 3.5 wt. %.

26. The process of claim 21 wherein the water concentration in the reaction mixture ranges from about 0.1 wt. % to about 2.0 wt. %.

27. The process of claim 25 wherein carbon dioxide and methane are produced in the reaction mixture and wherein the space-time yield for the production of methane exceeds the space-time yield for the production of carbon dioxide.

* * * * *